United States Patent [19]

Joishy

[11] Patent Number: 4,698,057
[45] Date of Patent: Oct. 6, 1987

[54] BUILT IN ASSEMBLY FOR STABILIZING AND SECURING INTRAVASCULAR NEEDLE OR CATHETER LIKE DEVICE

[76] Inventor: Suresh K. Joishy, 413 W. Howe St., Bloomington, Ind. 47401

[21] Appl. No.: 875,883

[22] Filed: Jun. 9, 1986

[51] Int. Cl.⁴ ............................................. A61M 5/00
[52] U.S. Cl. .................................. 604/176; 604/177; 604/180; 128/DIG. 26
[58] Field of Search .............. 604/176, 174, 177, 179, 604/180, 164; 128/DIG. 26

[56] References Cited

U.S. PATENT DOCUMENTS

| 3,490,442 | 1/1970 | Streu | 128/643 |
| 3,640,275 | 2/1972 | Burke et al. | 604/177 |
| 4,170,993 | 10/1979 | Alvarez | 604/180 |
| 4,324,236 | 4/1982 | Gordon | 604/180 |

Primary Examiner—Stephen C. Pellegrino
Attorney, Agent, or Firm—Woodard, Emhardt, Naughton Moriarty & McNett

[57] ABSTRACT

An assembly of built-in dual system for rapidly stabilizing and firmly securing an intravascular needle or catheter like instrument to a patient is disclosed. One portion of the system consists of a roll of adhesive tape fixed strategically in a wing like structure on each side of the needle or catheter. The second system is composed of built-in suction cups undersurface of a wing like structure on each side of the needle or catheter. Upon insertion of the needle, in a blood vessel of a patient, merely dabbing the wings of the catheter to the skin extrudes air out of the suction cups. Thus vacuum created causes the suction cups to cling to the skin immediately due to atmospheric pressure. As a result the wings and the needle are stabilized immediately. This frees the hands of the operator to uncoil the adhesive tape roll provided with a clip and handle device for easy grip. Each wing is taped down firmly to the skin, achieving permanent securement to the patient.

20 Claims, 14 Drawing Figures

BUILT IN ASSEMBLY FOR STABILIZING AND SECURING INTRAVASCULAR NEEDLE OR CATHETER LIKE DEVICE

FIELD OF THE INVENTION

The present invention relates to intravascular needle or catheter like surgical instrument, generally used to administer intravenous fluids and specifically used to administer chemotherapy drugs to the cancer patient and the method of stabilizing the same immediately after emplacement in a vein and achieve securement to the patient permanently.

BACKGROUND OF INVENTION

Placement of a surgical needle or catheter like device in the blood vessel for therapeutic or diagnostic purpose is a widely used method in the medical practice. Once the needle or catheter is emplaced in the blood vessel, it requires to be kept in place for a duration of the therapeutic or diagnostic procedure which may take a few minutes or several hours to a few days. Keeping the same needle or catheter in the same blood vessel properly secured for any length of time is by no means an easy task. The main problem with a needle or catheter is the ease with which they get displaced with slightest movement causing interruption of the procedure or even injury to the patient. There are several reasons for the displacement. First, the needle or the catheter requires insertion in the most mobile parts of the body, such as the hands or arms. Second, all the securing devices designed so far rely heavily on adhesive tape systems. Third, the tape systems can become non adherent easily, depending upon the method they are fastened, the amount of tape used, the body temperature, skin moisture and mobility of the part of the body they are fastened.

Administration of chemotherapy drugs through a needle or catheter inserted into a vein is one of the most widely used therapeutic approach in the treatment of the cancer patients. Proper securement and stabilization of the needle or catheter is of paramount importance in this situation because chemotherapy drugs are highly vesicant. If they extravasate into the skin as a result of displacement of needle or catheter considerable injury and morbidity to the patient may result.

Existing methods of improving the securement of the needle or catheter are still inadequate and techniques for improving are still sought after and still being proposed.

DESCRIPTION OF THE PRIOR ART

When a needle or catheter is emplaced in a blood vessel of a patient, it's connections are usually taped to the patient by means of adhesive tapes of various lengths and widths. The most popular is the V shaped tape wound around the hub of the needle or the catheter, also called the "Chevron Taping Technique". This technique is time consuming, varies in the final configuration, and reliable only to the extent of the operators experience. The adhesive tapes are plagued with problems. It is difficult to find the correct width of a tape roll. One needs to grope for the free edge of the tape roll which again is hard to unroll. Once you get the strips of tape cut to the length you desire, it is difficult to hold them free as they will cling to any surface on the slightest touch. The several delicate maneuvers or movements required for taping themselves, may dislodge the needle or catheter, sometimes injuring the blood vessel.

In an effort to overcome these short comings and to improve aspects of catheter securement designs the following list of patents disclosed designed features which have been conceived.

| U.S. PAT. NO. | PATENTEE | ISSUE DATE |
| --- | --- | --- |
| 1. 2,008,340 | SALVATI, A. T. and SALVATI, A.A. | July 16, 1935 |
| 2. 3,064,648 | BUJAN, A. F. | Nov 20, 1962 |
| 3. 3,885,560 | BALDWIN, B. F. | May 27, 1975 |
| 4. 4,324,236 | GORDON, M and LICHTENSTEIN, J. | Apr 13, 1982 |
| 5. 3,973,565 | STEER, P. | Aug 10, 1976 |
| 6. 4,059,105 | CUTRUZZULA, J and SHATTNER, R. L. | Nov 22, 1977 |
| 7. 4,049,141 | LACKO, M. A. and BROOKS, M. J. SPRANCER, D. M MITCHELL, P. P. | Dec 25, 1984 |
| 8. 4,170,993 | ALVAREZ, M. | Oct 16, 1979 |

It was first conceived by Selavti and Alceste in 1935 that some aid is needed to secure the needle or catheter besides tapes and bandages as they described in U.S. Pat. No. 2,008,340. A metallic plate was attached to the needle with brackets to insert tapes or bandages for securement. The drawback of this device is an elaborate metallic plate which was not part of the needle and it was not easy to pass tapes or bandages through the brackets.

Bujan disclosed in U.S. Pat. No. 3,064,648 an important improvement with mobile plastic flpas on each side of the needle which served not only as a needle holding device but helped the tapes to be fastened over them to the skin. However, the tapes did not necessarily stick firmly to the plastic flaps and one still has to be ready with strips of reinforcing tapes prior to the insertion of the needle or catheter and there is no standarad way of securing the wing flaps.

Baldwin in U.S. Pat. No. 3,885,560 described an elaborate folding bandage attached to the handle of the needle with adhesive surface protected by peel off paper. The main drawback of this device is too many movements required to peel off the protective adhesive paper and the assumption that all the bandages will stick to the skin. Hence, it has not been in popular use.

Gordon and Lichtenstein in U.S. Pat. No. 4,423,236 added further improvements in the wings of the catheter by designating a second pair of foldable wings underneath the main wings, having an adhesive undersurface to cling to the skin soon after insertion of the catheter. However, it had the same drawback of its predecessors, requiring delicate movements of peeling off of the protective layer of paper from the adhesive surfaces and the assumption that the plastic wings with the adhesive surface will cling to the skin, which rarely happens.

Further inventions were followed by designs of external adhesive tape devices of various sizes and shapes and flaps. Steer in U.S. Pat. No. 3,973,565 described a flap of adhesive tape attached to the rear part of the wings of the catheter. These were folded forward and taped to the skin after removing the adhesive protective layer. The drawback has been delicate movements to peel off the adhesive protective layer and a flap of tape obscuring the needle attachment to the skin, in which case, extravasation of the medication could not be visualized. Cutruzzula and Schattner in U.S. Pat. No.

4,059,105 improved the design with external flaps of adhesive tapes and with flap going back over the catheter but still obscuring the same. Finally, Lacko, in U.S. Pat. No. 4,049,141 designed external flaps of tapes which secured the catheter without hiding the insertion site or the connections. However, peeling off the several protective adhesive layers of papers and unreliability of their stickiness and requirement for reinforcement with regular tape proved to be of no advantage over the devices of his predecessors.

Alvarez in U.S. Pat. No. 4,170,993 was first to describe a roll of tape on each side of the external wing device. However, his assembly was too cumbersome and he failed to mention how the roll of tape was attached to the wings and how one can unroll them without dislodging the whole roll of tape. Thus, there exists a great need for a standard and easy way to apply a device to secure a catheter by means other than adhesive tapes alone. It is to this extent that the presenting invention is directed.

OBJECTIVES OF THE INVENTION

The object of the invention is to provide a built-in assembly of fittings which can be used to provide a rapid and standardized technique for stabilizing an intravascular catheter and permanently securing the same to the patient's skin subsequent to the emplacement of the needle or catheter. It is further the objective of the invention to provide the intravascular needle or catheter with manually manipulable wings on each side with suction cups undersurface. Dabbing the wings to the skin creates vacuum in the suction cups, making the wings hold the skin, with the aid of atmospheric pressure.

Another objective of the invention is to provide the intravascular needle or catheter fitting with a roll of tape on each wing which allows the needle or catheter to be rapidly secured to the skin upon unrolling the tape and taping down the wings on the surface of the skin. It is an additional objective of the feature of the invention to provide mobility of the roll of adhesive tape with a device to easily secure the free edge of the tape for unrolling rapidly and for securing the device firmly to the skin.

Still, a further objective of the invention is to provide an adhesive tape roll with a mechanism to unroll it easily with a moving roller to save the effort in securing the needle or catheter device firmly to the skin. Still, a further objective of the invention is to provide an assembly of the kind of referred securing device which is relatively simple and economical to manufacture from readily available materials. Obviously, it is the objective of this device to add convenience and safety to administer chemotherapy drugs through a needle or catheter.

SUMMARY OF THE INVENTION

A fitting for using intravascular emplacement of a needle or catheter like instrument comprises the catheter and needle on one end of the hub which to be attached to a connecting fluid line. Stabilizing wings extend laterally, one on each side of the hub. Preferably the hub and wings are entirely molded in a suitable plastic material and the wings can fold up and down independently above the hub for easy grip. This can be achieved by a hinge type arrangement substantially along the line of attachment of these wings with the hub by reducing the molding thickness along this line. The shape of the wings can take any suitable form convenient to facilitate manipulation but the surfaces are specially designed. The undersurface consists of tiny rubberized suction cups which not only gives comfortable friction to the skin, minimizing slipping, but also help the wings hold the skin by atmospheric pressure when the vaccum is created in the suction cups by pressing them down.

The upper surface of the wing is designed to slope down laterally where upon the wing thickness starting 2 mm near the hub will taper down to .1mm or less to prevent forming a gap between the skin and adhesive tape coming over the skin.

A specially designed roller assembly is provided in the medial aspect of each wing, close to the hub, fitting snugly in the gap of the wing. The adhesive tape is rolled over a metallic roller. The inner edge of the tape is fused to the metallic roller and the outer edge of the tape is fused with a specially designed handle which upon holding and pulling will easily release the tape from the roller to secure the wings down over the skin of the patient. The tape can roll friction free over a smooth stainless steel rod fitted in the gap of the wing. The wings have raised edges anteriorly and posteriorly so the adhesive tape will not be displaced over the wings even if they become slightly loose.

In use, the needle of the catheter is first inserted in the acceptable blood vessel when the operator is certain that it is emplaced inside the blood vessel, the wings on each side of the hub of the needle are dabbed down firmly on the skin and this creates vaccum in the tiny suction cups. Upon release of the pressure by removing the fingers away from the wings, the suction cups tend to re-expand and in doing so creating a vacuum inside. The atmospheric pressure will immediately fix the cups securely to the skin thus stabilizing the wings and in turn freed the operators hands for unrolling the tape for additional taping. This is done by gripping the free edge of the roll of the tape fixed on each wing and drawing the tape outwards. As it unrolls easily, the tape is firmly secured to the upper surface of the wings as well as over the skin for considerable distance lateral to the wings. The procedure is identical for securing wings on each side of the tub. The securing system of this invention does not obscure the needle insertion site in front ot the tubing connections behind the hub. If the drug to be administered takes only a short duration, no further securement is required. If the emplacement requires several hours to days one can reinforce the wings with more strips of tape.

In summary, this invention overcomes many inconveniences of existing catheter securing devices. First, there is a new methods of stabilization of the wings on the catheter, using suction cups. Second, the immediate stabilization of the catheter wings to the skin offers considerable freedom of the operators hands until complete securement is achieved. Third, the additional securing device and the adhesive roller tape is already built in the catheter system and one may not need to look for tape elsewhere. Fourth, it will be easy to get ahold of the free edge of the tape with specially designed handle fused to the outer edge of the tape and unroll the tape friction free. Fifth, it saves time and money in cutting the strips of tape, often of uncertain size and shape.

This device is most useful when the catheter emplacement is required for a few minutes such as administering cancer chemotherapy drugs by intravenous push, in which case no additional securement tapes are needed.

DESCRIPTION OF THE PREFERRED EMBODIMENT

Figure 1:
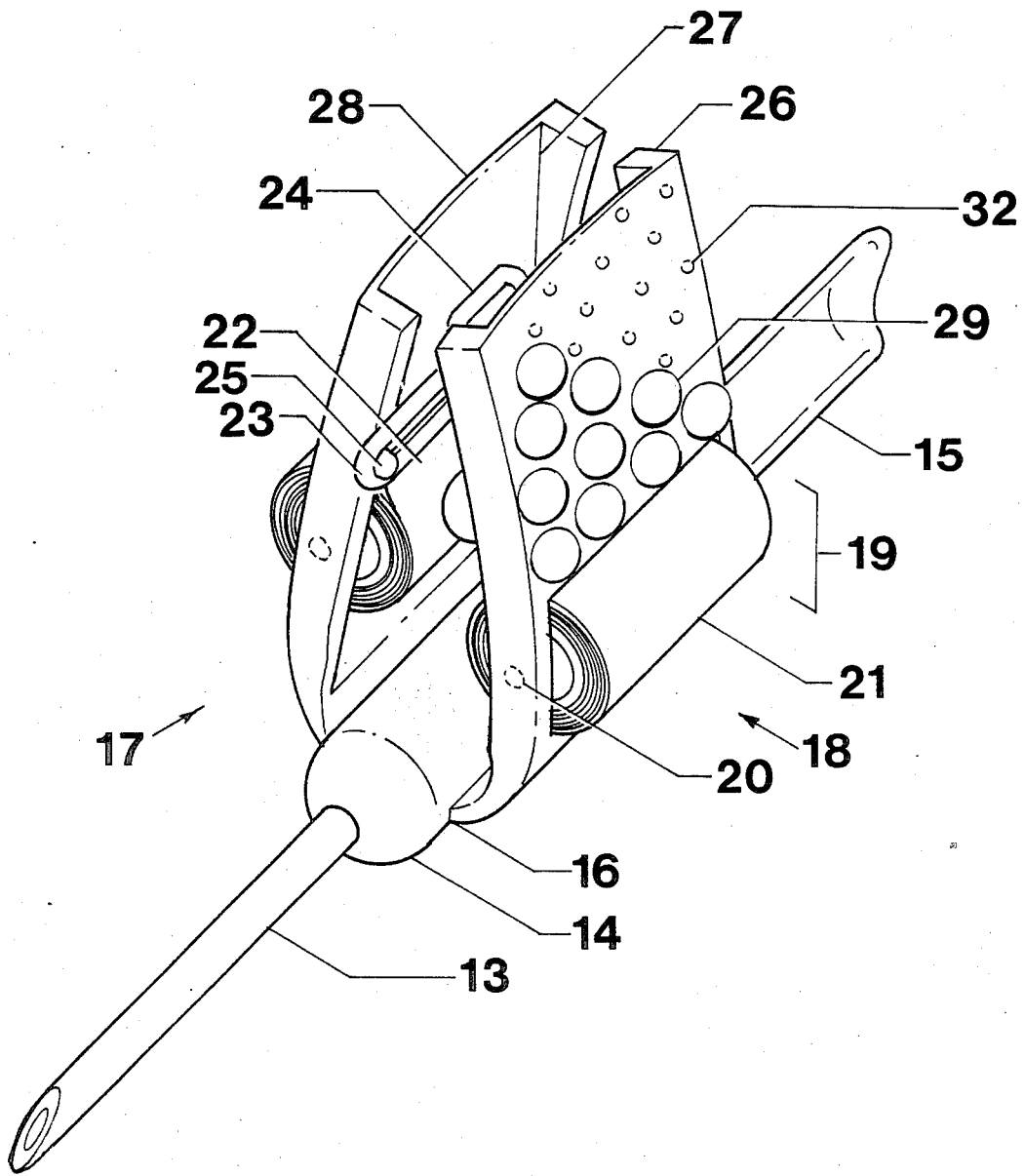
FIG. 1 is a prospective view of the intravascular needle with built-in assembly of stabilizing and securing devices, according to a typical embodiment of the present invention.

For the purpose of promoting and understanding the principles of the invention, reference will now be made to the embodiment listed in the drawings and specific language will be used to describe the same. It will nevertheless be understood that no limitation of the scope of the invention thereby intended, such alterations and further modifications in the illustrated device, such further applications of the principles of the invention as illustrated therein being contemplated as would normally occur to one skilled in the art to which the invention relates.

Figure 2:
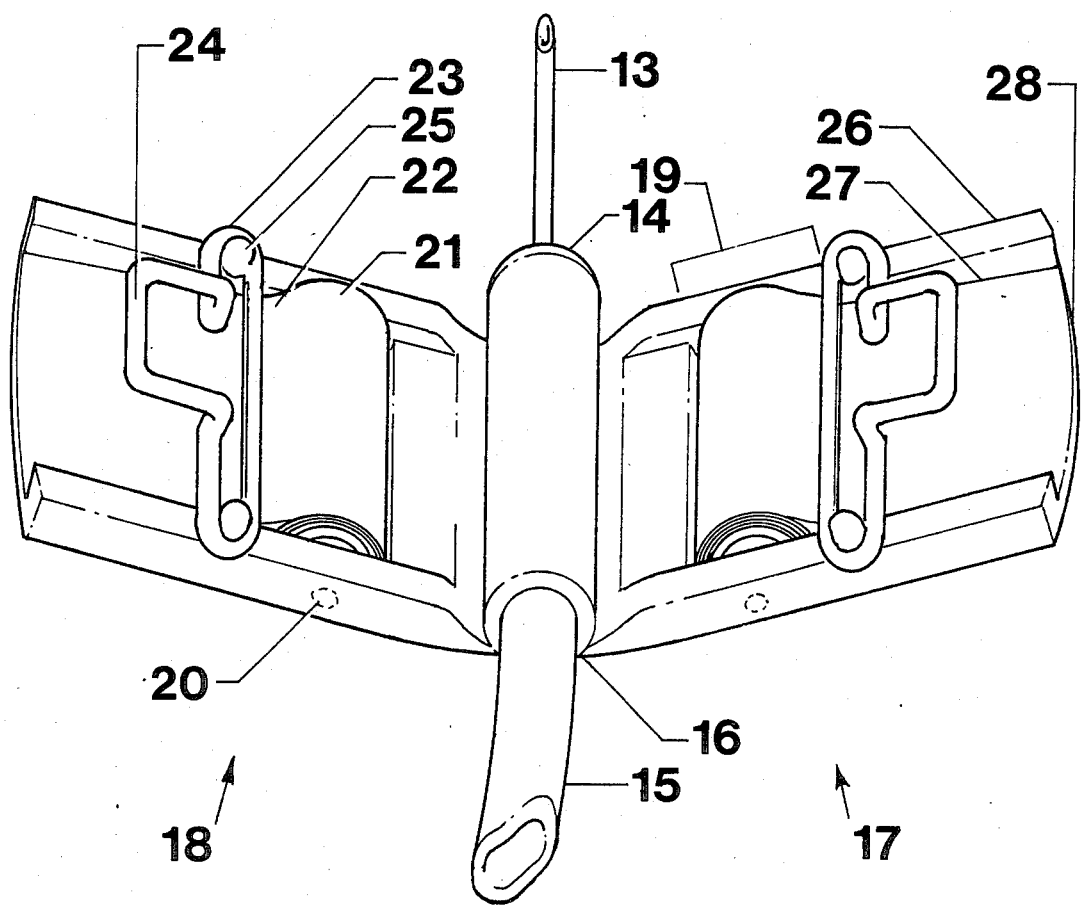
FIG. 2 is a view of the preferred embodiment from behind and above as the operator will see it, with a built-in assembly of stabilization and securing devices in resting position.
Figure 4:
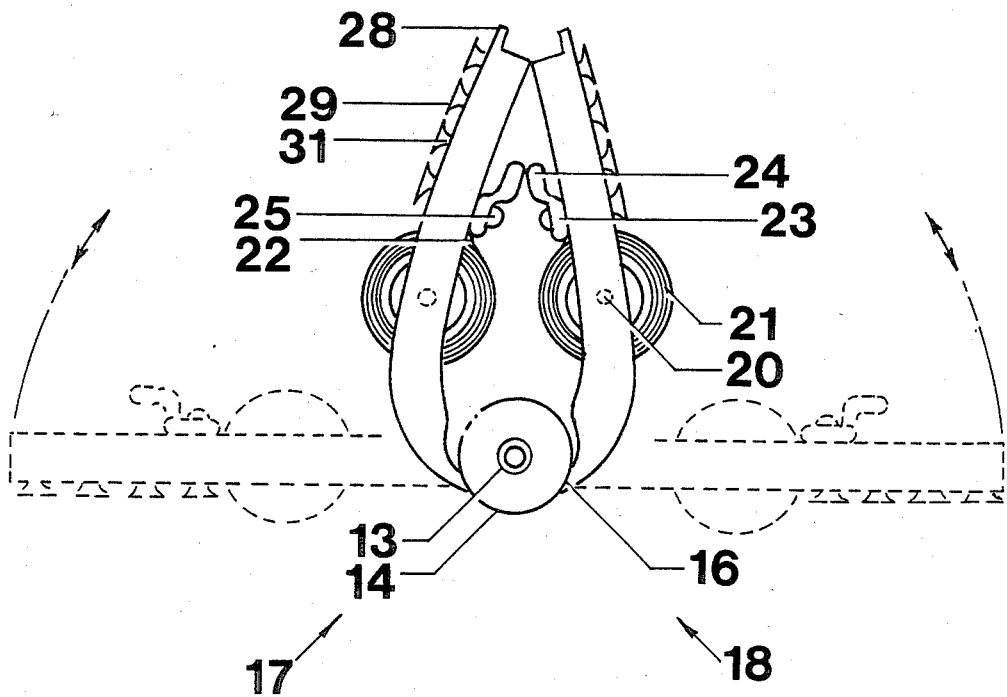
FIG. 4 is a frontal view of the embodiment illustrating movements of the wings with the assembly of stabilizing and securing devices.

Referring the FIG. 1 and 2 there is illustrated an intravascular needle 13 encircled by a hub 14 connected to a catheter 15. These structures are similar in size and shape and general configuration to intravascular needle or catheter devices in use. The hub is integrally molded with laterally extending wings, the right wing 17 and the left wing 18. The wings are made up of polyehtylene or like pliable material. They are 2 mm thick but molded to be thin to 0.2 mm attachment to the hub as to make them more pliable at the junction for mobility forming a hinge 16. FIG. 4 illustrates the moving position of the wings. The wing dimension may extend 2.5 cm from the hub laterally and 2 cm between the anterior and posterior borders.

Figure 3A:
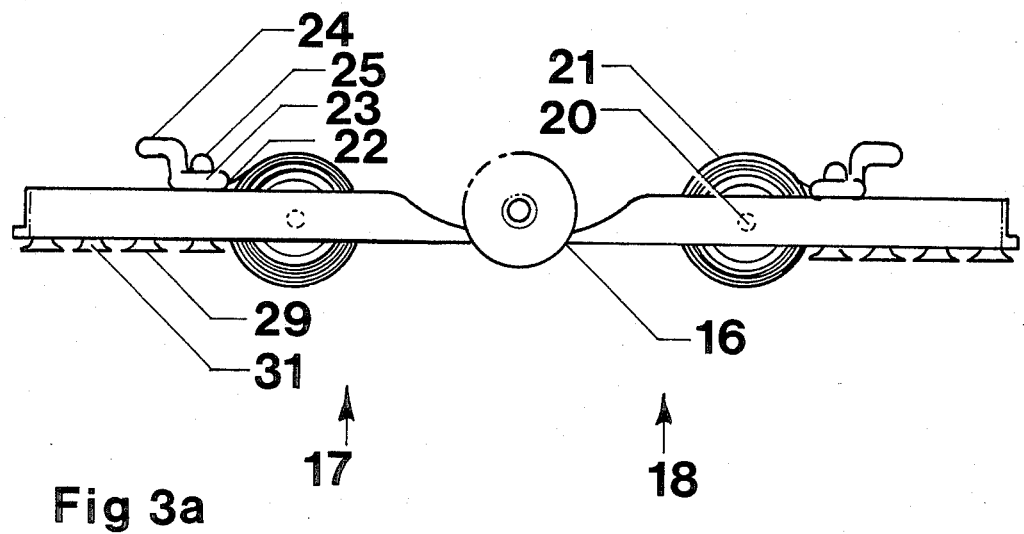
FIG. 3a is a frontal view of the embodiment with the wings showing stabilization and securing devices.
Figure 3B:
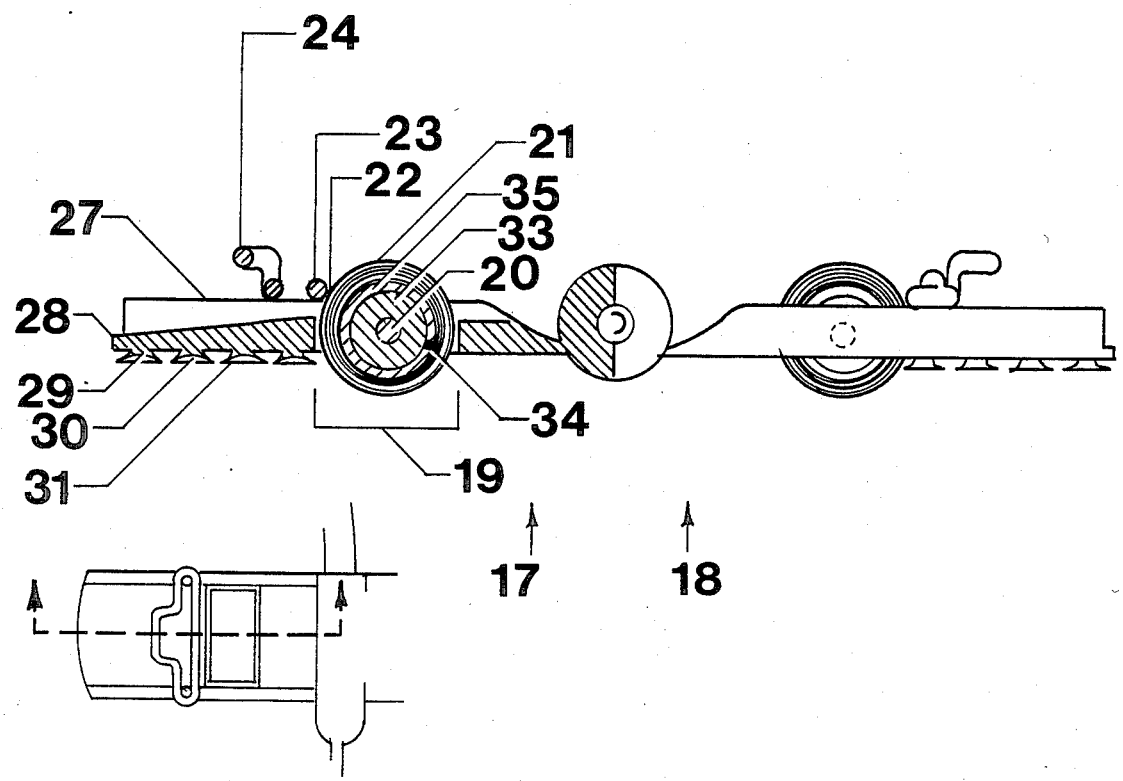
FIG. 3b is a sectional view of the right wing assembly comprising the adhesive roller tape mechanism.
Figure 6:
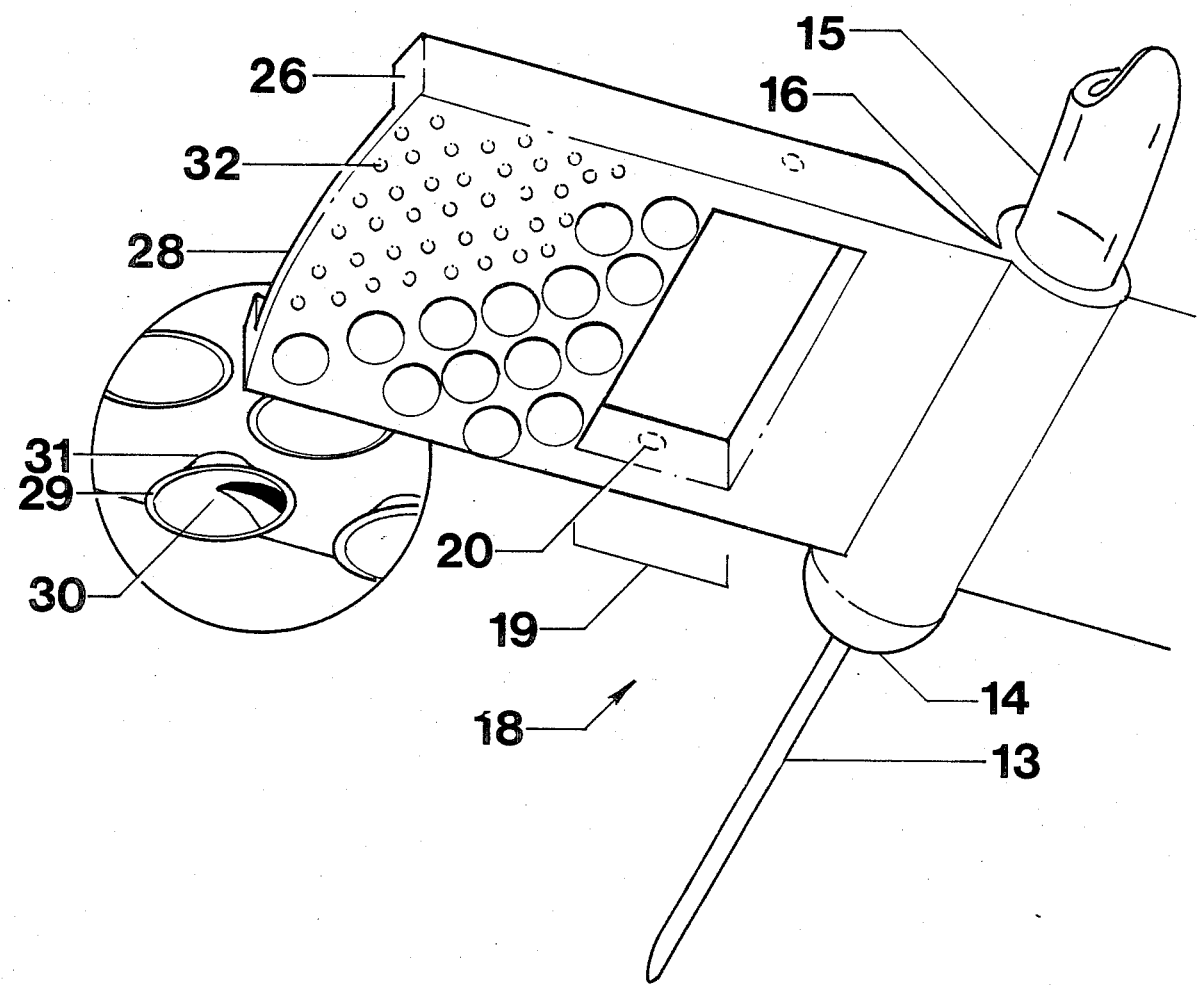
FIG. 6 is the undersurface of the left wing showing the suction cups. The detailed view of the suction cups is shown in the circular blown up picture.
Figure 7:
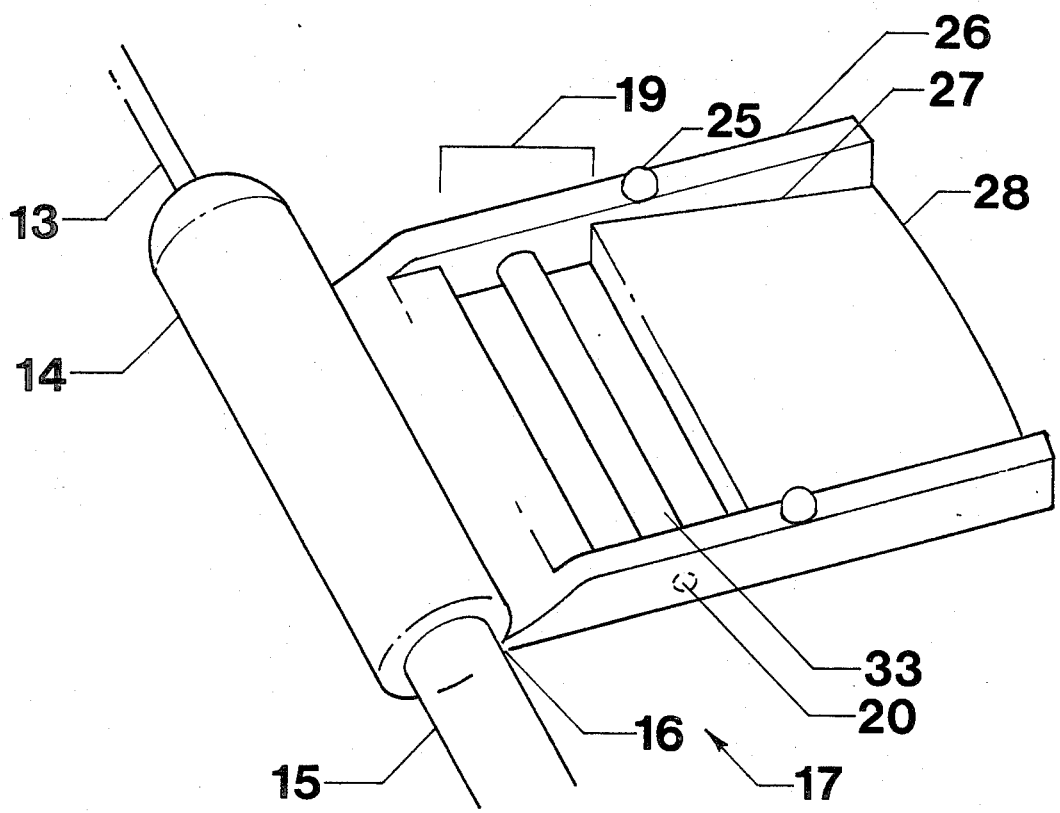
FIG. 7 is a mold of the right wing skeleton, showing the gap for tape roller assembly, the roller rod and positions of the tape, retaining knobs on the margins of the upper surface of the wing.
Figure 8:
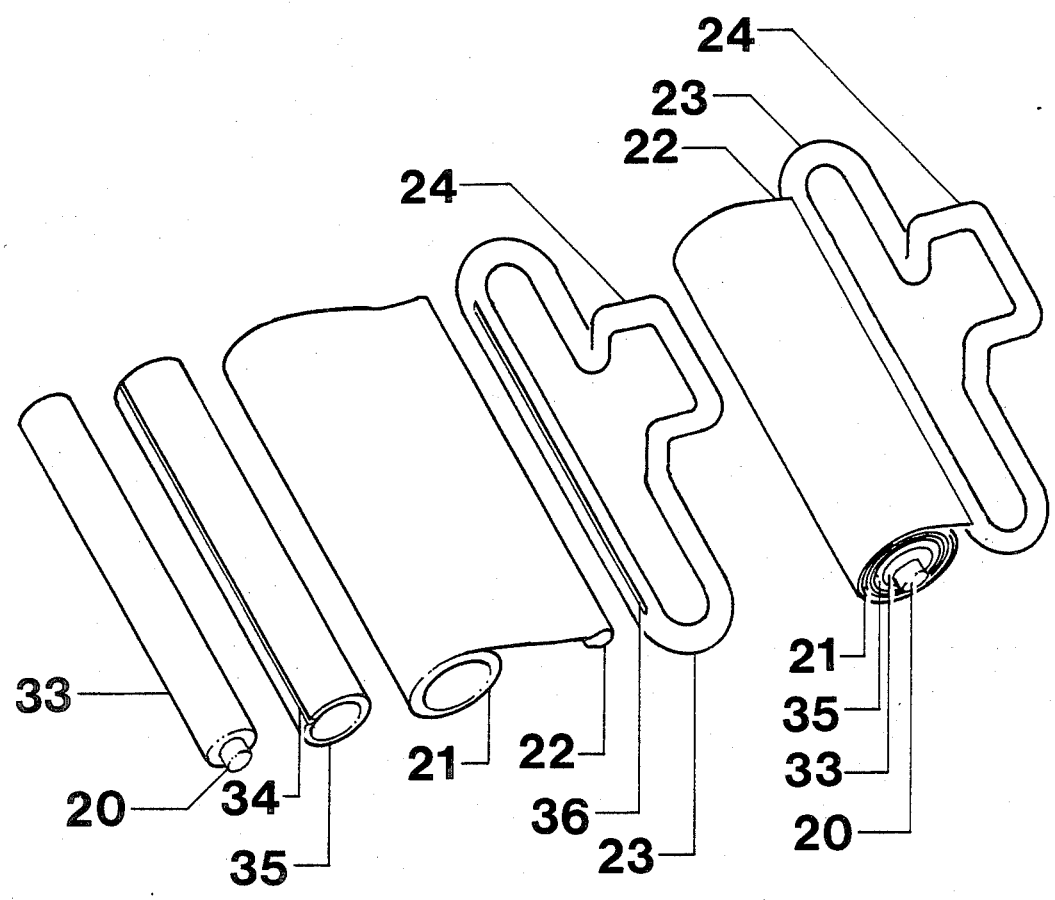
FIG. 8 shows the dissected parts of the asdhesive tape roll assembly, illustrating the positions of tape attachment to the roller and the handle.

Each wing carries a built-in adhesive tape roll 21 snuggly fitting in the wing gap 19 clearly shown in FIGS. 6 and 7. The tape roll 21 is placed strategically so as to cover at least three fourths of the upper surface of the wing when the tape is unrolled. FIGS. 3a, 3b and 8 illustrate the adhesive tape roll apart. A metallic rod 33 is fixed in the center of the wing gap 19 with the axis 20 fixed to the anterior and posterior portion of the wing margin. The rod is preferrably made of stainless steel with extremely smooth surface for the circular motion of the metallic roller 35. The metallic roller 35 is a stainless steel hollow cylindrical object with a diameter sufficient to just roll around the axis rod with freedom. It contains a longitudinal slit 34 in which the inner end of the tape roll 21 is fused securely.

Figure 5:
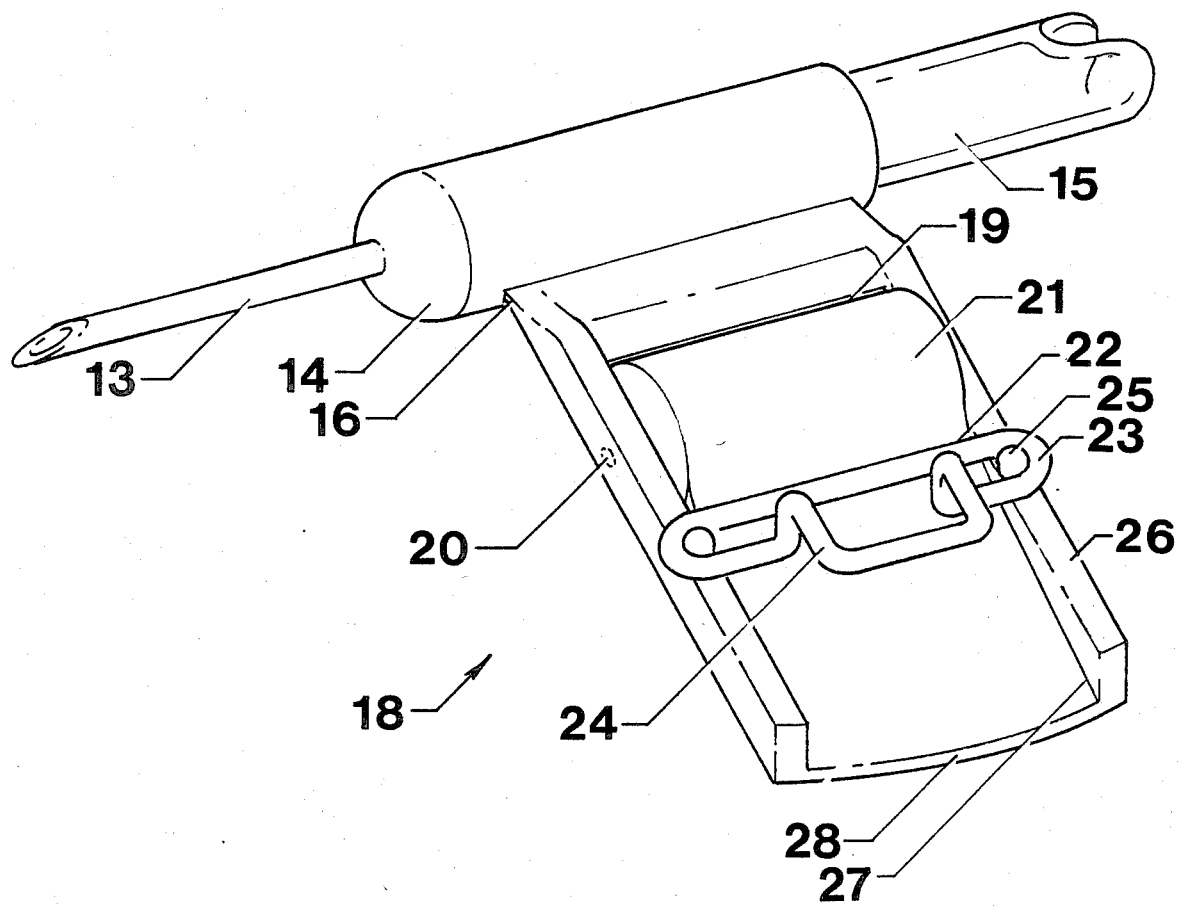
FIG. 5 is a lateral and superior view of the left wing assembly, illustrating the upper surface of the wing and the positions of the roller tape and its handle in relation to the wing.

The tape roll is made up of a very thin silk or hypoallergenic paper material that will not tear with stretching movements. Its dimensions are such that it is as wide as the metallic tape roller and when completely extended, it may stretch up to 5 cm. not only to cover the superior surface of the wing but also to extend sufficiently to be secured to the skin of the patient. The outer edge of the tape roll is fused in a longitudinal slit 36 in the inner arm of a metallic clip like device 23. The outer arm of the metallic clip 23 is bent upwards and outwards in such a way as to form a handle 24 to grip the entire clip, as shown in FIGS. 2, 5 and 8.

Figure 9A:
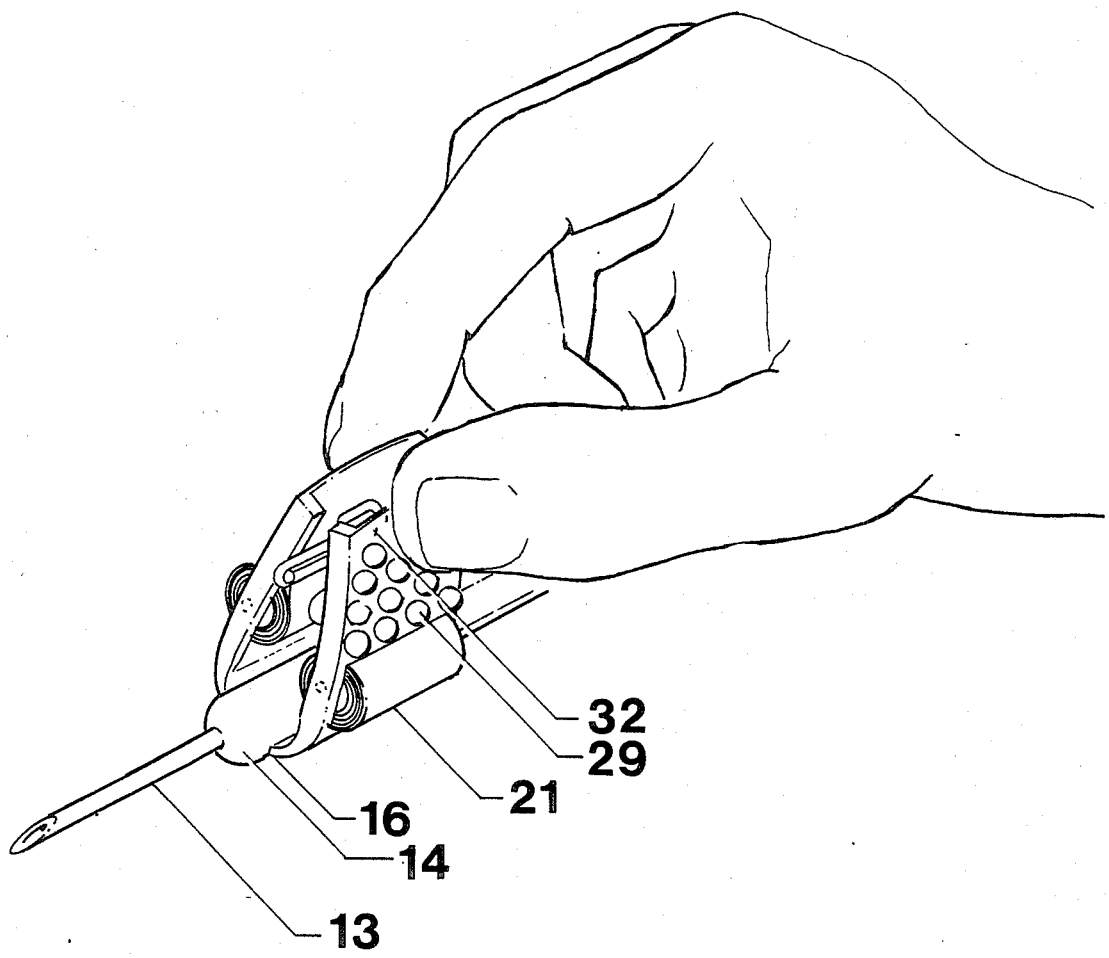
FIG. 9a illustrates the holding position of the embodiment by the operator, prior to insertion of the needle in a blood vessel.
Figure 9B:
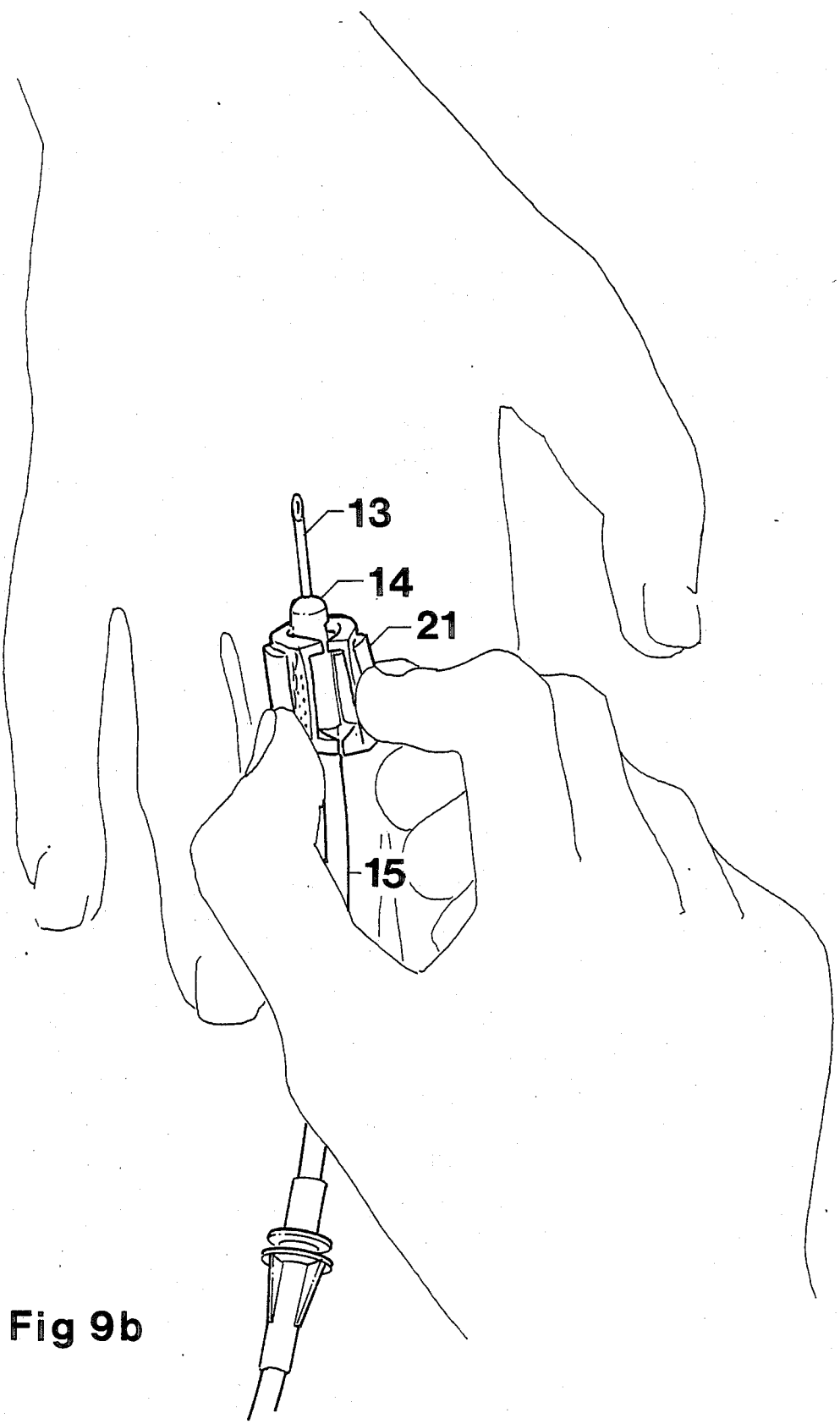
FIG. 9b shows the approach of the embodiment with needle towards the patients blood vessel.

The parts of the adhesive roller assembly shown in FIG. 8 are further defined in a cross sectional view of wing 17, shown in FIGS. 3b. The relative positions of the tape roller structures are a central axis 20 of the rod 33, surrounded by metallic roller 33 with a slit 34 to which the inner end of the tape is attached. The outer edge of the tape 22 is attached to the clip 23 which has a slit 36 and handle 24. FIGS. 6 and 7 illustrate the skeleton of the wings, showing the structures molded to receive the assembly of stabilizing and securing devices of the embodiment. FIG. 7 shows the structures on the superior surface of the right wing 17. The wing skeleton starts out lateral to the hub 14 with the mold thinned out to make it more pliable to form a hinge 16 so that the wing can move up and down as shown in FIG. 4, which facilitates holding of the embodiment for use as shown in FIG. 9a and 9b. Close to the hub, a wing gap 19 is cut out from the mold to receive the tape roll assembly shown in FIGS. 1 through 5. At the center of the wing gap, the metallic rod is fixed at the axis 20 around which the metallic roller for the tape can slide in a circular motion easily and the adhesive tape may be unrolled. Lateral to the wing gap the upper surface 27 of the wing is designed to slope down steeply between the margins 26 as to form a thin outer rim 28 also shown in FIGS. 1, 2, 5 and 6. The sloping and thin margin facilitates the adhesive tape to fasten the wings flush with the skin without a gap between the wings and the skin. It should be noted that as a result of the sloping of the upper surface of the wing the margins 26 are elevated. The helps to keep the tape fit snuggly on the upper surface of the wing and at the same time movement of the tape or the wing will not cause the tape to become dislodged from the wings. On the surface of the elevated margins anteriorly and posteriorly, the mold forms a knob 25. These knobs help to fit the anterior and posterior loops of the clip 23 snuggly in its resting position, until the operator lifts a handle 24 up prior to unrolling the tape. The left wing skeleton is molded identically and its undersurface is shown in FIG. 6. Starting from the hub to the wing gap, the undersurface is flat and smooth. Lateral to the wing, however, cup like structures are placed which firm the stabilizing structures of the embodiment. An array of suction cups are placed in a triangular area anteriorly as shown in FIG. 1 and FIG. 6. The suction cups are magnified in a circular inset, in FIG. 6. Each suction cup has a rim 29, a concave surface 30, looking down and the cup attached to the undersurface of the wing with pedicle 31. A suction cup is made up a rubberized plastic material, with a rim extremely thinned out. Due to the pliability, the gentle pressure of the wings to the skin extrudes air out. At the same time the thinned out rim forms an effective seal around the cups, creating a vacuum inside when the pressure on the wings is released. This causes atmospheric pressure to force the cups against the skin, thus stabilizing the entire wing assembly to the skin surface. Again due to the pliability and thin margins of the cups, gentle lifting of the wing is sufficient to lift the cups from the skin surface, avoiding any injury to the skin. The triangular surface posterior to the cups is molded to contain tiny studs 32. The area containing the studs help the operator to hold the entire wing assembly between the thumb and index finger as shown in FIG. 9a and 9b and the studs helping to create friction and easy grip between the fingers.

The entire embodiment with relative positions of all the structure described so far is shown in FIGS. 1 and 2, with identical structures on each wing assembly. In summary, the hub 14 encircles the needle in front and the catheter connection 15 behind. The wing assembly is attached laterally at the junction 16. The wing gap 19 contains the adhesive tape roll with the free outer edge 22 affixed to the clip 23 with the loops of the clip resting on knobs 25. The outer arm of the clip is elevated to form a handle 24. The superior wing surface 27 is sloped down to form a thin outer rim 28 so that the margins 26 appear elevated to fit the tape snuggly after securement. The undersurface of the wing, lateral to the tape assembly, contains suction cups for stabilization in the anterior triangle and studs for holding the embodiment.

Figure 10:
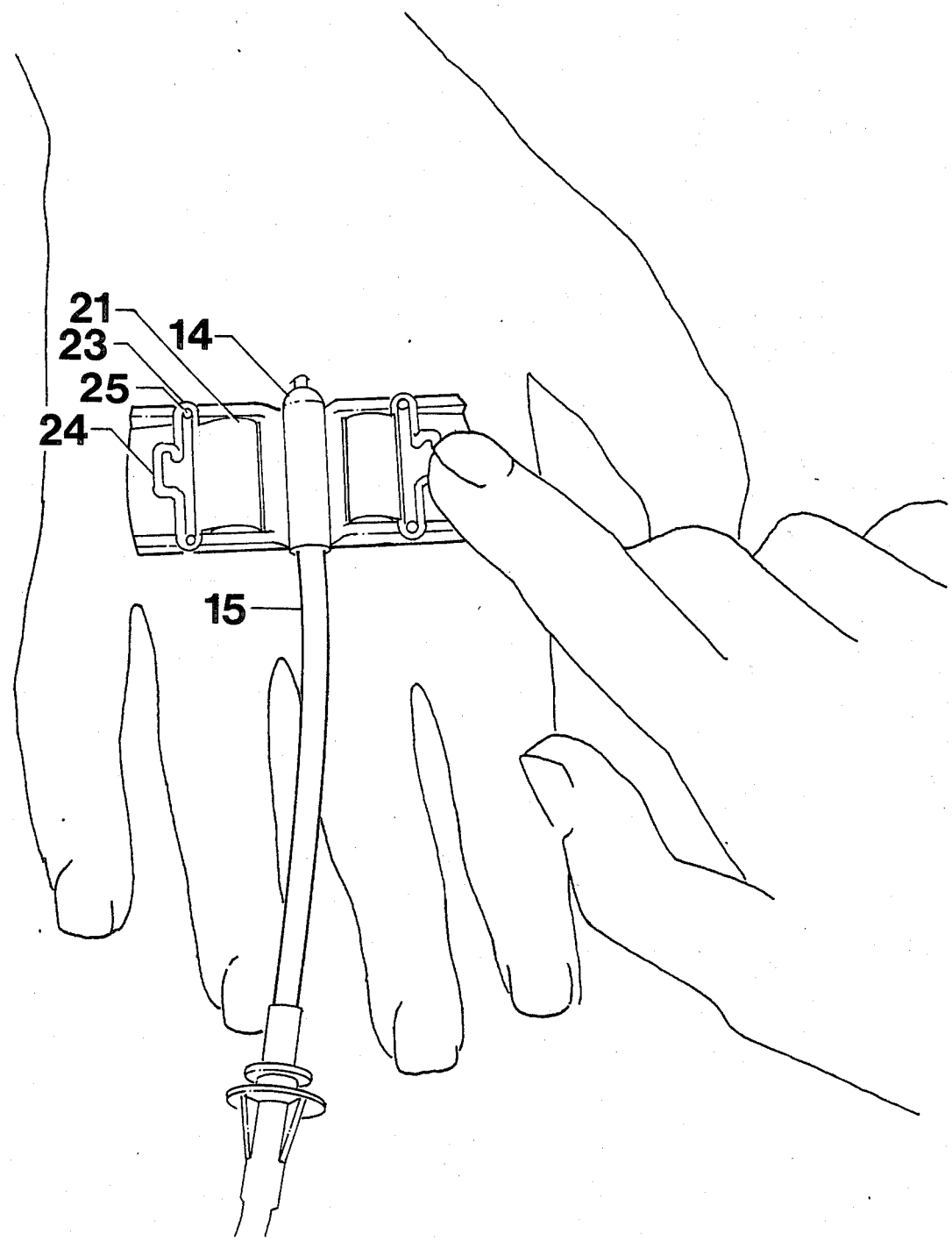
FIG. 10 shows the position of the wings after insertion of the needle and the operator dabbing the wings to the skin to extrude the air out of the suction cups for stabilization of the wings due to atmospheric pressure.
Figure 11:
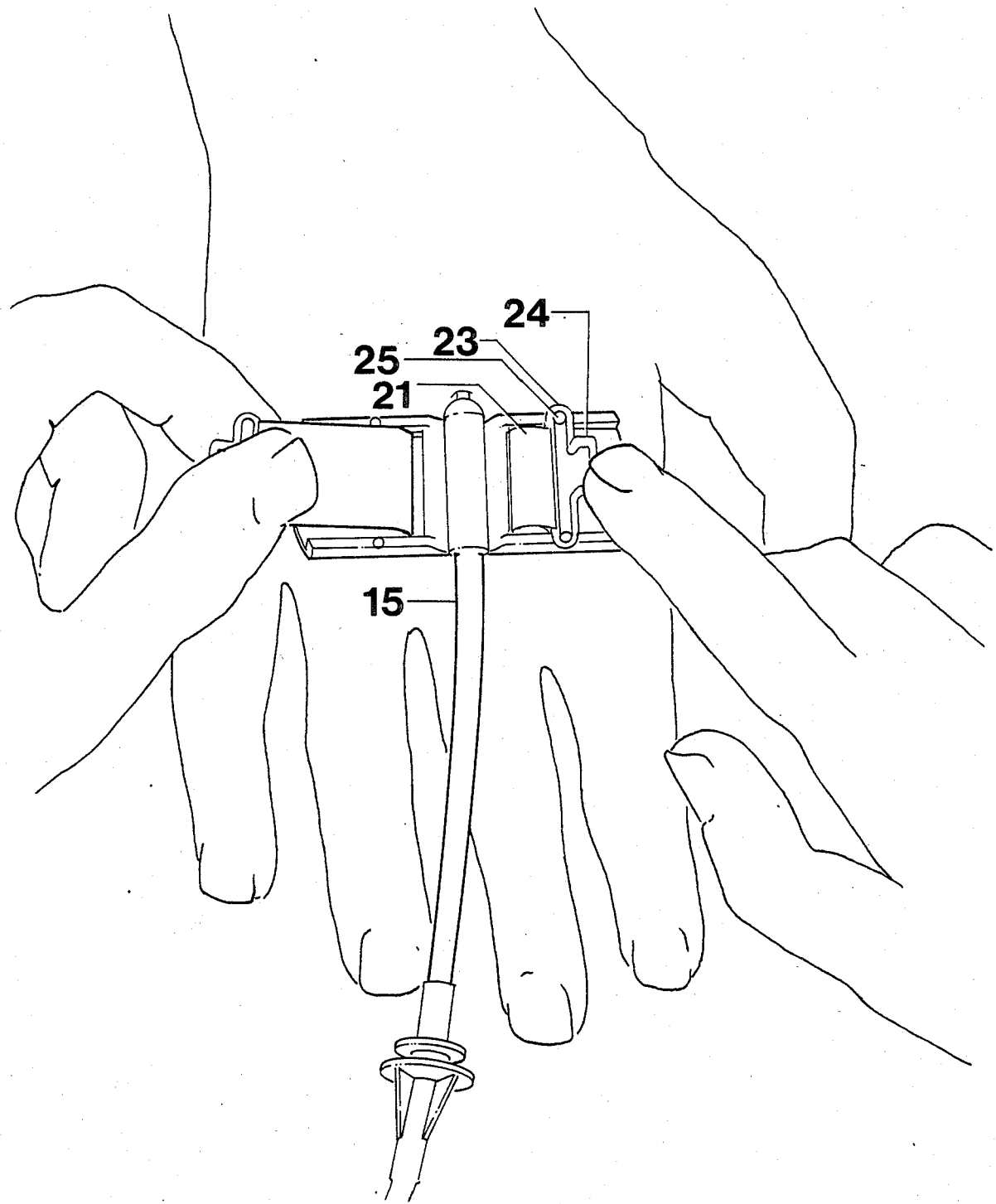
FIG. 11 shows unrolling of the tape using the handle at the outer edge of the tape.
Figure 12:
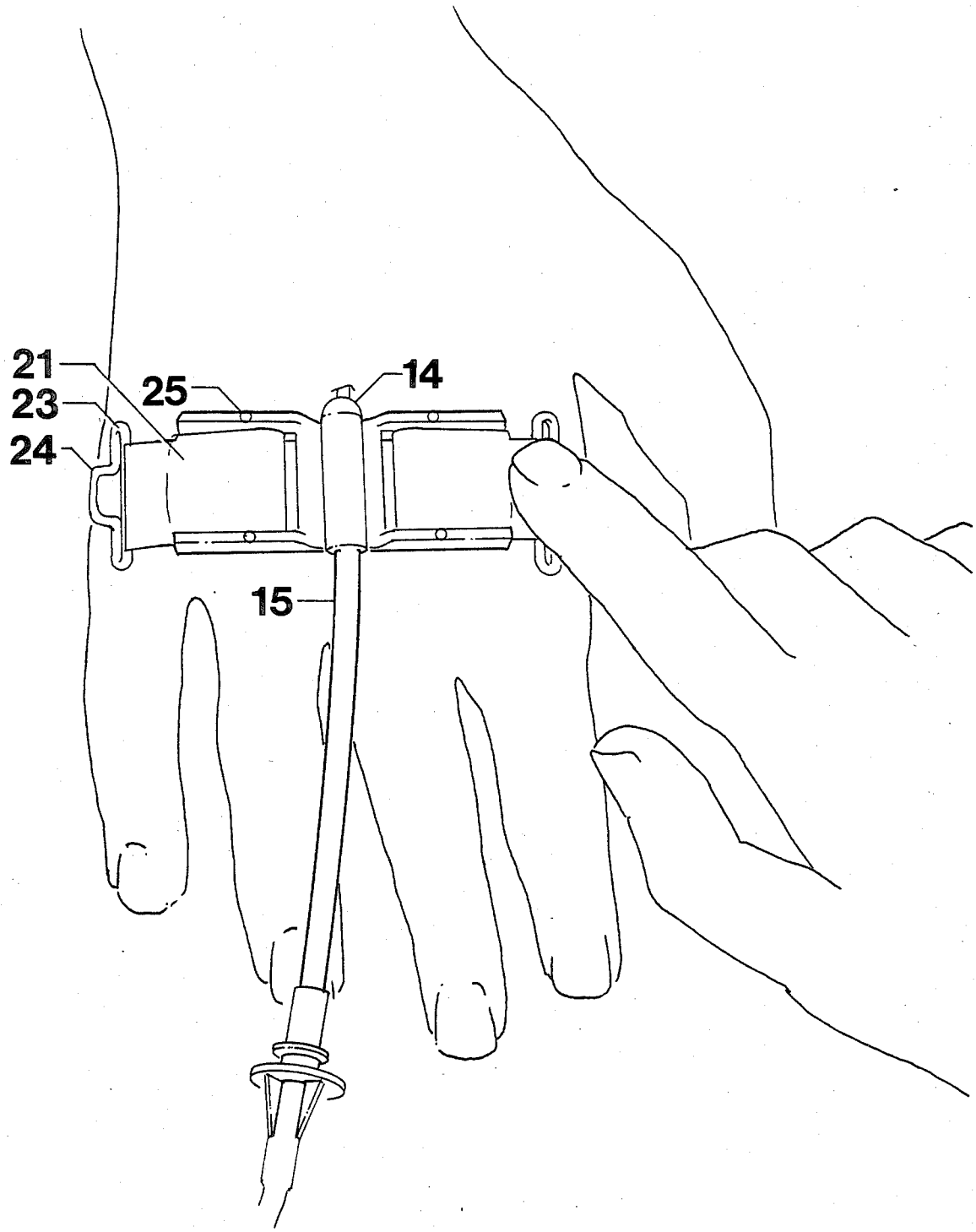
FIG. 12 shows completion of the operation of securement of the intravascular device to the patient's skin.

FIG. 9 through 12 illustrates the sequential steps of using the embodiment with its needle assembly and its stabilizing and securing devices. FIG. 9a shows how an operator, a nurse, technician or a physician can hold the embodiment with the wings folded up conveniently between the thumb and index finger. The triangular undersurface contains studs designed to help create friction between the fingers and the wing for a firm grip. In FIG. 9b the intravascular needle is about to penetrate the patient's vein, and it should be noted here that there is absolutely no obstruction of the view of the needle by the embodiment of the tape assembly. In FIG. 10 the needle 13 has penetrated the skin, and soon after the operator has confirmed the emplacement of the needle in the vein, the right and left wing 17 are laying flat on the skin surface. The operator is dabbing the right wing against the skin of the patient gently. This procedure extrudes air out of the suction cups underneath the wing, creating a vacuum and the rims of the suction cups cling firmly to the skin, creating vacuum inside the cups. As a result, atmospheric pressure forces the suction cups to the skin surface and the right wing is immediately stabilized. The same procedure is repeated to stabilize the left wing. At this stage the needle and the catheter and the wing assembly is stabilized to the skin without conventional tape attachment! This offers great freedom to the operator's hands now to further secure the device. With this invention the operator has no need to look around for tapes. The adhesive tape roll is already built in the wings. FIG. 11 describes how the operator can unroll adhesive tape to each wing. First, the free edge of the tape is disengaged from the wing by lifting the handle 24. In this situation there is no need to grope for the free edge of the tape, which is a usual problem with the conventional tape rolls. By pulling the handle gently with one sweeping lateral motion, the entire adhesive tape will be unrolled. In FIG. 11 the operator has already unrolled the tape in the left wing. Due to elevated margins 26 the tape snuggly fits in the upper surface of the wing and also glides smoothly over the skin due to the thin lateral rim 28 of the wing. Thus, the tape can be secured flushly with the wing as well as the skin, leaving minimal gap between the wing and the skin for tighter securement. The same procedure is repeated on the opposite wing and FIG. 12 shows how both wings have been tightly secured to the skin of the patient.

If the operator chooses the procedure requiring short duration, such as administration of chemotherapy drugs to the cancer patient, no further securement is required. However, now the operator has enough freedom and time if he chooses to use the device for a longer period of time by securing the entire embodiment with further tapes.

From the foregoing discussion it becomes clear that a intravascular needle or catheter device can be secured to the patient with minimal movements, minimal amounts of tape and the entire procedure is standardized because of built-in prefabricated structures, avoiding the need to search for outside devices. The attachment of the clip with the handle device to the free edge of the tape on an adhesive roll avoids the trouble of searching for the free edge of a tape and frustrating efforts of peeling the same, off the tape roll. Considerable freedom is offered to the operator by the suction cups that immediately stabilize the entire device so the operator can use both hands for further securement.

It should be understood that although an intravascular needle and catheter device has been illustrated with newly designed stabilizing and taping equipment, the various features of disclosed invention are equally well suited to work every type of intravascular device or catheter as well as any medical equipment that requires taping by adhesive tape. Other various materials and connection techniques are possible, the optimal materials and dimensions will depend on the part of the basic intravascualar needle or catheter style and other medical equipment as well as its intended application.

While the invention has been illustrated and described in detail in the drawings and the foregoing description, the same is to be considered as illustrated and not restrictive in character, it being understood only the preferred embodiment has been shown and described and all changes and modifications that come within the spirit of the invention are desired to be protected.

What is claimed is:

1. A device for stabilizing and securing an intravascular needle or catheter like surgical instrument to a patient, comprising:
    a tubular intravascular surgical instrument having a hub and laterally extending wings attached to each side of the hub, said wings having a stabilizing means for stabilizing the position of said surgical instrument relative to a patient receiving said instrument, said stabilizing means including
    a plurality of suction cups on the undersurface of each wing,
    an adhesive tape assembly having a cylindrical roller rotatably mounted to said one of the wings on the superior surface thereof and a roll of adhesive tape fixed at the inner end thereof to said cylindrical roller,
    a grasping means fixed to the outer end of said adhesive tape roll for facilitating the uncoiling of the tape roll, and
    a securing means extending from the superior surface of said one of the wings for securing the grasping means thereto prior to uncoiling of said type roll.

2. The device of claim 1 wherein said stabilizing means further includes
    a second adhesive tape assembly on the other of said wings having a second cylindrical roller rotatably mounted to the other of said wings on the superior surface thereof and a second roll of adhesive tape fixed at the inner end thereof to said second cylindrical roller,
    a second grasping means fixed to the outer end of said second adhesive tape roll for facilitating the uncoiling thereof, and
    a second securing means extending from the superior surface of the other of said wings for securing the second grasping means thereto prior to uncoiling of said second tape roll.

3. The device of claim 2 wherein said tubular intravascular surgical instrument further includes studs on the undersurface of each of the wings posterior to said suction cups for aiding the grasping of the wings between thumb and index finger of the operator.

4. The device of claim 3 wherein each of said grasping means includes a looped wire clip and handle integrally extending from said clip.

5. The device of claim 4 wherein said wings have gap recesses in the supereior surfaces thereof and said adhesive tape assemblies are mounted to said wings within said recesses.

6. The device of claim 5 wherein said wings taper laterally to define thin edges at the outer rims of said wings which engage flush with the skin of a patient thereby permitting continuous securement of said wings and the skin by the adhesive tape.

7. The device of claim 6 wherein each of said wings have raised anterior and posterior margins sufficiently spaced apart to permit placement of said adhesive tape therebetween thereby preventing anterior or posterior displacement of said adhesive tape after securement.

8. The device of claim 7 wherein said suction cups are made of a pliable polyethylene material, said suction cups having concave and thin outer rims facilitating sealing to the skin after extrusion of air therefrom, each of the suction cups further having pedicles attached to the undersurface of the wings permitting slight sliding movements of the suction cups thereby further facilitating extrusion of the air therefrom in stabilizing said wings to the skin of a patient.

9. The device of claim 8 wherein said securing means includes raised knobs on the anterior and posterior margins of each of said wings and said clips are sized to secure in press fit over said knobs.

10. The device of claim 9 wherein said tubular intravascular surgical instrument is a catheter.

11. The device of claim 9 wherein said tubular intravascular surgical instrument is a needle.

12. A device for stabilizing and securing an intravascular needle or catheter-like surgical instrument to a patient, comprising:
    a tubular intravascular surgical instrument having a hub and laterally extending wings attached to each side of the hub, said wings having a stabilizing means for stabilizing the position of said surgical instrument relative to a patient receiving said instrument, said stabilizing means including
    a plurality of suction cups on the undersurface of each wing,
    an adhesive tape assembly having a cylindrical roller rotatably mounted to each of said wings on the superior surface thereof and a roll of adhesive tape fixed at the inner end thereof to each said cylindrical roller,
    a grasping means fixed to the outer end of each said adhesive tape roll for facilitating the uncoiling of the adhesive tape roll,
    each of said wings having raised anterior and posterior margins sufficiently spaced apart to permit placement of said adhesive tape therebetween thereby preventing anterior or posterior displacement of said adhesive tape after securement, said wings tapering laterally to define thin edges at the outer rims of said wings which engage flush with the skin of a patient thereby permitting continuous securement of said wings and the skin by the adhesive tape.

13. The device of claim 12 wherein said tubular intravascular surgical instrument further includes studs on the undersurface of each of the wings posterior to said suction cups for aiding the grasping of the wings between thumb and index finger of the operator.

14. The device of claim 12 wherein said stabilizing means further includes
    a grasping means fixed to the outer end of each said adhesive tape roll for facilitating the uncoiling thereof, and
    a securing means extending from the superior surface of each of said wings for securing the grasping means thereto prior to uncoiling of said adhesive tape rolls.

15. The device of claim 14 wherein each of said grasping means includes a looped wire clip and handle integrally extending from said clip.

16. The device of claim 12 wherein said wings have gap recesses in the superior surfaces thereof and said adhesive tape assemblies are mounted to said wings within said recesses.

17. The device of claim 12 wherein said suction cups are made of a pliable polyethylene material, said suction cups having concave surfaces and this outer rims facilitating sealing to the skin after extrusion of air therefrom, each of the suction cups further having pedicles attached to the undersurface of the wings permitting slight sliding movements of the suction cups thereby further facilitating extrusion of the air therefrom in stabilizing said wings to the skin of a patient.

18. The device of claim 11 wherein said securing means includes raised knobs on the anterior and posterior margins of each of said wings and said clips are sized to secure in press fit over said knobs.

19. The device of claim 12 wherein said tubular intravascular surgical instrument is a catheter.

20. The device of claim 12 wherein said tubular intravascular surgical instrument is a needle.

* * * * *

UNITED STATES PATENT AND TRADEMARK OFFICE
CERTIFICATE OF CORRECTION

PATENT NO. : 4,698,057

DATED : October 6, 1987

INVENTOR(S) : Suresh K. Joishy

Page 1 of 2

It is certified that error appears in the above-identified patent and that said Letters Patent is hereby corrected as shown below:

Column 2 line 33; change the word "flpas" to --flaps--

Column 2 line 39; change the word "standarad" to --standard--

Column 3 line 2; delete the word "and"

Column 6 line 1; change the word "polyehtylene" to --polyethylene--

Column 6 line 65; after the word elevated change the word "The" to --This--

Column 7 line 9; after the word "wing" insert the word --gap--

Column 7 line 10; change the word "firm" to --form--

Column 7 line 17; after the word "up" insert the word --of--

Column 8 line 11; change the word "to" to --on--

Column 9 line 24; change the word "type" to --tape--

Column 9 line 64; after the word "concave" insert the word --surfaces--

UNITED STATES PATENT AND TRADEMARK OFFICE
CERTIFICATE OF CORRECTION

PATENT NO. : 4,698,057

DATED : October 6, 1987

INVENTOR(S) : Suresh K. Joishy

It is certified that error appears in the above-identified patent and that said Letters Patent is hereby corrected as shown below:

Column 10 line 62; change the word "this" to --thin--

Column 11 line 1; after the word "claim" change "11" to --15--

Signed and Sealed this

Twenty-ninth Day of March, 1988

Attest:

DONALD J. QUIGG

Attesting Officer

Commissioner of Patents and Trademarks